(12) United States Patent
Crosby et al.

(10) Patent No.: US 6,813,958 B2
(45) Date of Patent: Nov. 9, 2004

(54) METHOD FOR COMBINATORIALLY MEASURING ADHESION STRENGTH

(75) Inventors: Alfred J. Crosby, Alexandria, VA (US); Eric J. Amis, Bethesda, MD (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 121 days.

(21) Appl. No.: 10/174,933

(22) Filed: Jun. 19, 2002

(65) Prior Publication Data

US 2002/0194930 A1 Dec. 26, 2002

Related U.S. Application Data

(60) Provisional application No. 60/299,782, filed on Jun. 21, 2001.

(51) Int. Cl.[7] ................................................. G01L 1/24
(52) U.S. Cl. ........................................ 73/800; 73/150 A
(58) Field of Search .............................. 73/800, 150 A, 73/760, 774, 776, 789, 809, 827, 862.041, 862.042, 862.043, 862.044, 862.045, 862.046, 775

(56) References Cited

U.S. PATENT DOCUMENTS

| | | | |
|---|---|---|---|
| 3,548,652 A | | 12/1970 | Beatty et al. |
| 4,194,392 A | | 3/1980 | Lombard et al. |
| 5,298,366 A | | 3/1994 | Iwasaki et al. |
| 5,300,263 A | * | 4/1994 | Hoopman et al. ........... 264/2.5 |
| 5,333,494 A | | 8/1994 | Kishima et al. |
| 5,453,876 A | | 9/1995 | Hamada |
| 5,493,926 A | | 2/1996 | Vines et al. |
| 5,992,226 A | | 11/1999 | Green et al. |
| 6,026,680 A | | 2/2000 | Mann |
| 6,030,917 A | | 2/2000 | Weinberg et al. |
| 6,045,671 A | * | 4/2000 | Wu et al. .............. 204/298.11 |
| 6,157,449 A | | 12/2000 | Hajduk |
| 6,175,409 B1 | | 1/2001 | Nielsen et al. |
| 6,178,823 B1 | | 1/2001 | Sykes |
| 6,180,739 B1 | | 1/2001 | Bowen |
| 6,182,499 B1 | | 2/2001 | McFarland et al. |
| 6,308,560 B1 | | 10/2001 | Bracht |
| 6,513,374 B2 | * | 2/2003 | Goh et al. ................ 73/150 A |

FOREIGN PATENT DOCUMENTS

| | | |
|---|---|---|
| EP | 0 582 437 | 2/1994 |
| JP | 5-288725 | 11/1993 |

OTHER PUBLICATIONS

Feature Article—Axisymmetric adhesion tests of soft materials, Kenneth R. Shull et al., Macromol. Chem. Phys. 199, 489–511 (1998).

* cited by examiner

*Primary Examiner*—Edward Lefkowitz
*Assistant Examiner*—Corey D Mack
(74) *Attorney, Agent, or Firm*—Butzel Long

(57) ABSTRACT

A method of measuring the adhesive strength of polymer materials that are arranged in a combinatorial library which involves providing a lens array having a plurality of individual lens elements on a surface thereof and a substrate. A pattern of different polymer materials, processing variables or environmental conditions is applied to either the individual lens elements of the lens array or to the substrate. The individual lens elements of the lens array are brought into contact with the substrate and, as the lens array and substrate are separated from one another, changes in contact area of the individual lens elements with the substrate are monitored and used to calculate the adhesive strength of the polymer.

17 Claims, 3 Drawing Sheets

METHOD FOR COMBINATORIALLY MEASURING ADHESION STRENGTH

RELATED APPLICATION

This application is based upon and claims priority to United States Provisional Patent Application Serial No. 60/299,782, filed Jun. 21, 2001 and entitled "Method for Combinatorially Measuring Adhesion," the complete disclosure of which is hereby expressly incorporated by reference.

TECHNICAL FIELD

The present invention relates to a method of measuring the adhesive strength of polymers interfaces. More particularly, the present invention is directed to a method of measuring the adhesive strength of polymers interfaces in a combinatorial manner.

BACKGROUND ART

The adhesion strength (or weakness) of polymeric materials is a critical property for numerous technologies. For example, in electronic packaging, polymeric materials are used as thermal insulator layers, electrical insulator layers, or as binders between two non-adhesive material layers. In each of these cases, the mechanical integrity of the resulting electronic package is directly dependent upon the integrity of the polymer interfacial areas. Therefore, the surface properties as well as the bulk properties of the polymer layers must be properly chosen and/or engineered to maximize or achieve a desired or required degree of adhesion strength for a given environment of a particular electronic package. In some applications, minimizing the adhesive properties of polymer layers may be required rather that maximizing the adhesive properties. An example of the latter application is a biomedical device that is required to be resistant to contamination. One method of controlling contamination of such biomedical devices is to use a properly engineered polymer coating that minimizes the adhesion between the polymer and common, targeted or suspected contaminants. This process of minimizing the adhesion between the polymer and common, targeted or suspected contaminants must be performed so that the adhesion is at the same time optimized for the operating conditions or environment of the biomedical devices.

Given the wide range of physical requirements and end-use environmental conditions, finding an optimal polymer, i.e., one that has or can be engineered to have desired or required adhesive properties for a particular substrate, can be a difficult, time consuming task, since a reliable theory for general polymer interfacial strength does not exist. The efficiency of finding the best polymer material(s) is ultimately limited by the inefficiency of existing adhesion tests. These adhesion tests are not only inefficient, but the results of many of them are unreliable.

Many companies such as Symyx Technologies of Santa Clara, Calif. are developing instruments to use combinatorial methods to aid in materials discovery and characterization. For example U.S. Pat. No. 6,030,917 to Weinberg et al. discloses methods and apparatus for screening catalysts. U.S. Pat. No. 6,175,409 to Nielsen et al discloses flow-injection analysis and variable-flow light-scattering methods and apparatus for characterizing polymers. U.S. Pat. No. 6,182,499 to McFarland et al. discloses systems and methods for characterization of materials and combinatorial libraries with mechanical oscillators. U.S. Pat. No. 6,157,449 to Hajduk discloses depolarized light scattering array apparatus and methods of using the same. Although these U.S. Patents address properties and techniques that are important for the development of polymer technologies and demonstrate the growing interest in combinatorial measurement techniques, they do not provide a method for characterizing properties that are directly related to the adhesive strength of polymer interfaces.

U.S. Pat. No. 5,477,732 to Yasue e al., U.S. Pat. No. 4,137,761 to Miller, U.S. Pat. No. 5,144,845 to Pyke, U.S. Pat. No. 3,548,652 to Beatty et al., and U.S. Pat. No. 4,194,392 to Lombard et al exemplify various techniques and instruments that have been developed for measuring polymer adhesion. Each of the techniques disclosed in these patents makes a quantitative measurement of the adhesive strength of a polymer interface. However, the measured quantities are only truly useful as relative measures of adhesion and therefore, the measurements from these techniques cannot be correlated with physical properties of the contacting materials.

To make quantitative, absolute measurements of adhesive strength, more laborious techniques are commonly used. Two accepted techniques for these measurements include the flat punch probe tack test (ASTM 15.06; Creton, 2000) and the spherical probe, or JKR, technique (Johnson et al, 1971). Both probe techniques provide very quantitative measurements of polymer adhesion by using a single probe (either a flat punch or a spherical punch) to mechanically form and separate a polymer interface in a single test. Using fracture mechanics relations and the measured quantities of force and contact area or displacement and contact area, the adhesion energy of the interface can be quantified. Although accurate and quantitative, the efficiency of these procedures is limited due to the required analysis and the total time to complete a single test.

No existing technologies provide a means of conducting combinatorial investigations of polymer adhesion.

DISCLOSURE OF THE INVENTION

According to various features, characteristics and embodiments of the present invention which will become apparent as the description thereof proceeds, the present invention provides a method of measuring the adhesive strength of a polymer which involves:

providing a lens array having a plurality of individual lens elements on a surface thereof;

providing a substrate;

applying a polymer to at least one of the individual lens elements of the lens array or the substrate;

contacting the individual lens elements of the lens array with the substrate;

separating the lens array and substrate from one another while monitoring changes in contact area of the individual lens elements; and calculating the adhesive strength of the polymer at the contact area.

The present invention further provides a method for measuring the adhesive strength of polymer material interfaces that are arranged in a combinatorial library which involves:

providing a lens array having a plurality of individual lens elements on a surface thereof;

providing a substrate;

contacting the individual lens elements of the lens array with the substrate in a controlled manner while providing a parameter gradient there between and monitoring changes in contact area, said parameter gradient comprising at least one of a physical parameter, an environmental parameter and a material parameter; and calculating the adhesive strength of the polymer at the contact area.

BRIEF DESCRIPTION OF DRAWINGS

The present invention will be described with reference to the attached drawings which are given as non-limiting examples only, in which.

BEST MODE FOR CARRYING OUT THE INVENTION

Figure 1:
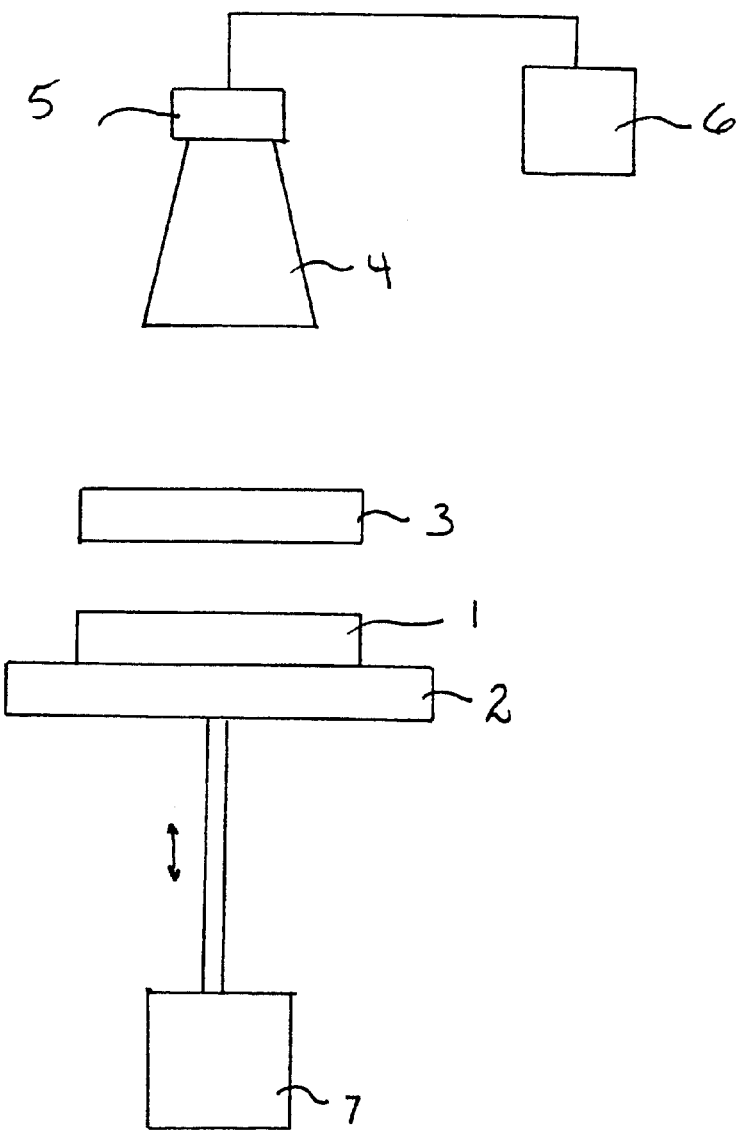
FIG. 1 is a schematic diagram of an apparatus which can be used according to one embodiment of the present invention.

The present invention is directed to a method for measuring the adhesive strength of polymer interfaces in a combinatorial manner. The method utilized according to the present invention applies to polymer-to-polymer interfaces, polymer-to-metal interfaces, and polymer-to-ceramic interfaces and is not limited to any specific polymer, metal or ceramic or any type of polymer, metal or ceramic. The combinatorial aspect of the test method according to the present invention allows for optimal conditions and/or compositions that will allow desired adhesive strength to be identified in a high-throughput, parallel manner. In addition to being useful for identifying optimal adhesion conditions experimentally, the method facilitates the identification of trends in adhesive behavior parameter space. The analyses of such trends are used to formulate predictive models that can guide the design of application-specific adhesive materials. Moreover, the described test method utilized provides a high-throughput quantitative characterization of polymer interfaces.

The present invention provides a method for measuring the adhesive strength of polymer materials that are arranged in a combinatorial library. As used and referred to herein, the combinatorial library includes of two parts: a periodic distribution of curved surfaces, such as a microlens array, and a complementary substrate. According to the method of the present invention, these two library components are brought into contact with each other under controlled displacement conditions. Upon contact, a combinatorial array of polymer interfaces is created between the two library components. As described in detail below, parameters are measured during and after the contact between the lens array and complementary substrate. The resulting information is used to produce a map of interfacial strength.

As noted above, the combinatorial library has two components. The first component comprises a periodic distribution of curved surfaces, such as a lens array, with specified bulk and surface properties. The second component comprises a complementary substrate also with specified bulk and surface properties. For illustrative purposes, a non-limiting example of the present invention will be described in which the periodic distribution of curved surfaces will be referred to as a lens array. However, it is to be understood that other periodic distributions of curved surfaces can also be used. Herein, the use of the term "lens array" is not meant to imply that the material of the lens array must be transparent. In the present invention it is the repeating shape of the curved surfaces that produces multiple contact points and multiple polymer interfaces. The transparency, non-transparency, opaqueness, or other light transmission properties of the lens array are not critical to testing polymer adhesive properties. It is also noted that the there is no particular restriction that the contacting surfaces of either or both the library components have to be parallel. In fact, other configurations may provide particular advantages. For example, non-parallel surfaces can be used to apply a gradient of applied strain along a selected axis. According to one experimental embodiment of the invention, an array of microlenses was provided on a convex surface of a substrate. In this configuration, the alignment of the two library components was not critical since the convex positioning of the microlens array was used to provide a convenient gradient in strain along radial axes.

Lens arrays with specified bulk and surface properties that are useful for purposes of the present invention can be produced using conventional techniques, such as the processes described in U.S. Pat. No. 5,300,263 to Hoopman et al. U.S. Pat. No. 5,298,366 to Iwasaki et al., and U.S. Pat. No. 5,453,876 to Hamada. In addition, a master mold of a lens array can be used to mold lens arrays. Each of the selected lens arrays to be molded, the master mold, and the reproduced molded lenses can all be produced by any known processes. The lens arrays can be molded or otherwise made from a wide variety of material compositions and properties. If a lens array is made from a material that does not possess desired surface properties, standard coating technologies can be used to modify the surface properties. After fabricating a lens array, the array can be fixed to a support substrate if desired. The complementary substrate can likewise be molded or formed using known technologies. The complementary substrate can be made from a desired material or coated with a desired material.

To test the adhesive strength between the individual lenses on the array and the material on the complementary substrate, the two library components are brought into contact. Upon reaching a predetermined degree of contact which can be monitored by measuring compression forces or displacement or contact area, the two library components are separated at a controlled displacement rate. During both the contact and separation processes, the contact area created by each contact point of the combinatorial array of polymer interfaces, i.e., the contact between the individual lenses and the planar surface of the complementary substrate, is recorded together with the corresponding displacement of each contact point. The recorded contact points and displacement information provide a contact history for each individual lens elements and are used to quantitatively determine the adhesion energy of the polymer interfaces. A qualitative mapping of the combinatorial array is obtained by imaging the contact points over the entire array. With this information, the conditions for optimal adhesion at a polymer interface can be determined as a function of the parameters varied in the combinatorial library. In addition to empirically determining optimal adhesion conditions for a specific application, this technique can be used in molecular engineering to optimize adhesive materials for industries such as, but not limited to, electronic packaging, biomaterials, and coatings.

FIG. 1 is a schematic diagram of an apparatus which can be used according to one embodiment of the present invention. The complementary substrate 1 is placed on a support 2 which can be moved vertically. The lens array 3 is held in a fixed position over the complementary substrate 1. An optical microscope 4 with a charged coupled device 5 (CCD) is position over the lens array 3 so as to observe and record contact area between the individual lens elements of the lens array 3 with substrate 1. The charged coupled device 5 is coupled to a computer 6 that is used to calculate and record the contact areas of the individual lens elements of the lens array 3.

The support 2 is moved vertically by a step motor 6 or other suitable mechanical means. Displacement during contact between the complementary substrate 1 and the lens array 3 can be monitored and controlled by a piezoelectric transducer.

In an alternative embodiment, the complementary substrate 1 can be held in a fixed position and the lens array 3 and the charged coupled device 5 can be moved by a step motor 7. It is also possible to provide an apparatus that moves either or both the complementary substrate 1 and the lens array 3 (together with the charged coupled device 5) horizontally.

In order to prevent interference in the tests results, the apparatus can be mounted or supported on vibration dampening table or vibration dampening support.

According to one embodiment of the present invention, a unique set of properties can be prescribed to each individual interface created during the contact of the individual lens elements with the complementary substrate by controlling the processing conditions of each lens element or the in situ test conditions of each lens element. For example, according to one embodiment of the invention, a polymer layer can be provided that has one or more gradients in multiple properties. An example of such a layer is a polymer blend layer that has a continuous gradient in composition along one axis and a continuous gradient in layer thickness in an orthogonal direction. By placing such a layer on the lens array or on the complementary substrate, each individual lens interface will be exposed to a unique combination of thickness and composition. According to another embodiment, coating or deposition techniques such as those used in inkjet technology could be used to modify the properties of interfaces in a discrete manner. For example, such deposition techniques, including those used in inkjet technologies, could be used to place unique compositions onto discrete areas of a lens mold, such as, for example, in individual wells of a lens mold or other area. Alternatively, such deposition techniques could be used to place unique compositions on discrete surface areas of a lens array, or on discrete surfaces of the complementary substrate.

In addition, or an alternative approach, to manipulating the physical properties, i.e. material properties and structure of the lens elements, it also possible to manipulate the test conditions to achieve different parameter gradients with respect to physical, material and environmental characteristics along a desired axial, radial and/or orthogonal direction. Examples of parameter gradients that can be manipulated broadly include physical, environmental and material parameters. More specific examples of parameter gradients that can be manipulated include, but are not limited to, temperature, surface energy, strain, rate of strain, molecular weight of a polymer used, surface topography, surface roughness, chemical functionality, metal coating composition, ceramic coating composition, etc. It noted that the testing procedures are not limited to occurring in air or other gaseous (inert or reactive) environment. It is also possible to conduct the testing in an aqueous or other liquid environment.

The two library components can be brought into contact and separated under various test and/or environmental conditions. That is, the degree of force contact between the lens array and the complementary substrate, the period of contact, the rate of contact and separation and other test parameters can be varied together with the ambient conditions such as humidity, temperature, gaseous environment, etc. It is to be understood that adhesive strength can also be qualified according to the present invention upon contact of the library components. That is, is not an necessary to separate the two library components in order to quantify adhesion energy. Measuring the adhesion energy upon contact and separation may actually yield different information.

Whether each interface is exposed to a different set of processing and/or environmental conditions, each test can produce a library of unique polymer interfaces that allows mapping of the interfacial strength based on its dependence on multivariable conditions within the time of a single test procedure. Calibration standards and replicate samples can also be included within the combinatorial array to aid in interpreting and verifying test results.

Figure 2:
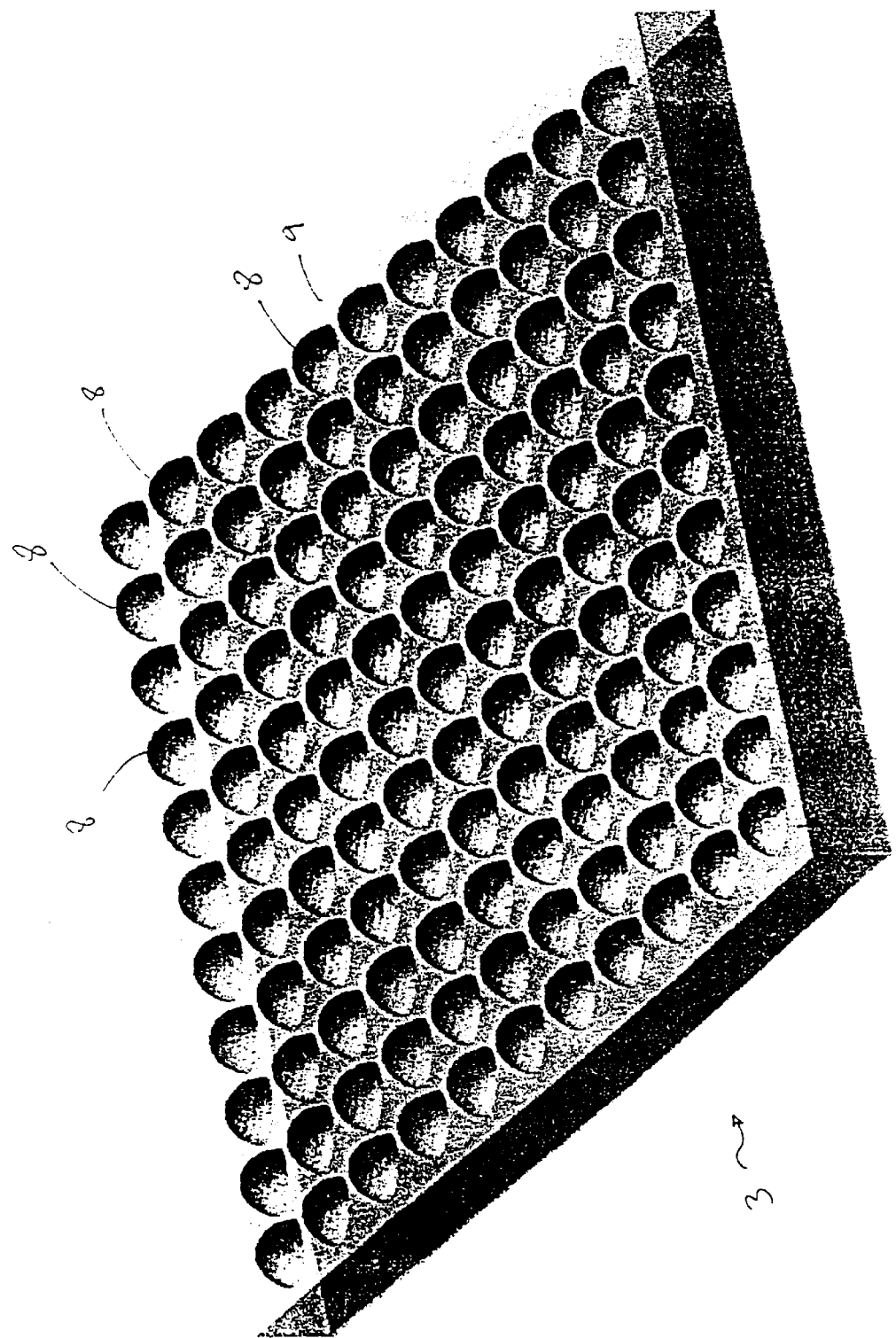
FIG. 2 is a perspective view of a lens array that can be used according to one embodiment of the present invention.

FIG. 2 is a perspective view of a lens array that can be used according to one embodiment of the present invention. The lens array 3 includes a plurality of individual lens elements 8 which project from one surface 9 thereof. The individual lens elements 8 can be semi-spherically shaped as depicted. Alternatively, the individual lens elements 8 can have any desired shape including frusto-conical, cylindrical, trapezoidal, frusto-pyramidal, etc. It is preferred that the upper surfaces of the individual lens elements 8 be convexly curved so that controlled changes in contact area are produced by small incremental changes in displacement.

Figure 3:
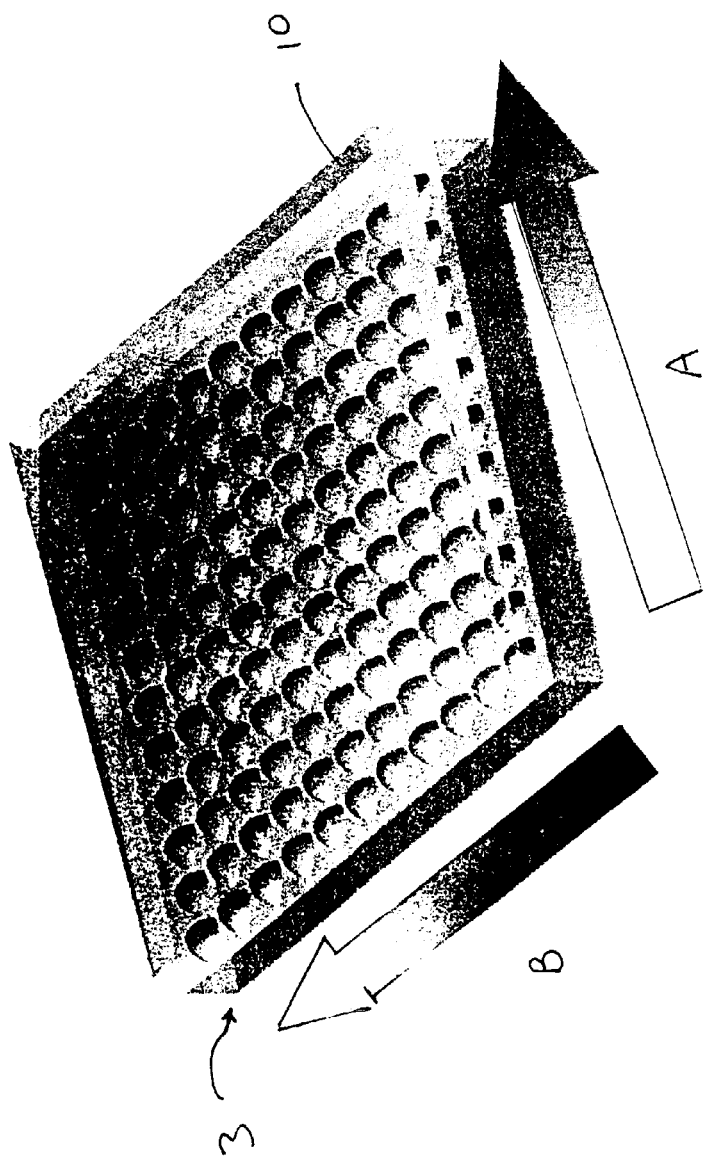
FIG. 3 is a perspective representation of one manner in which polymer gradients can be applied to a lens array according to one embodiment of the present invention.

FIG. 3 is a perspective representation of one manner in which polymer can be applied to a lens array according to one embodiment of the present invention. In FIG. 3 the polymer layer 10 which is actually applied in a uniform thickness to the lens array 3, is depicted as having an increasing thickness in the direction indicated by arrow A. In an orthogonal direction indicated by arrow B, the polymer layer 10 has an increased degree of shading which represents an increasing gradient of one of the components of the polymer. Combined, the thickness and gradient of the one component of the polymer provide a complete range of variations of the polymer which can be tested simultaneously according to the present invention.

According to the principles of the present invention, thousands of spherical probe tests can be completed in the same time that one such test it typically completed. For example, by using an array that contains 1600 lenses, a single test with such an array according to the present invention would result in the same quantity of data produced by 1600 individual adhesion tests. In terms of time, this example translates into collecting the same quantity of data conventionally produced in eighty days in a matter of minutes. The timesaving benefit includes both the actual testing time and the analysis time. For example, by monitoring the contact area distribution across the lens array, a qualitative mapping of relative adhesive strengths can be assessed quickly. In this qualitative, relative measurement, statistical error is minimized since the processing and pretest environmental conditions of each adhesion measurement site are uniform. In contrast, during conventional testing, relative measurements of adhesion are hindered by inconsistencies that can and often do exist between samples. The ability to qualitatively map relative adhesive strengths across the array allows for quick and efficient focus of quantitative analysis to the region(s) of parameter space that are of greatest interest to a specific application.

The present invention facilitates rapid screening of combinatorial polymer libraries for adhesive strength. The ability to conduct parallel processing and testing greatly enhances the identification of optimized interface combinations which can be used to establish and engineer or otherwise provide desired adhesive strength for a given application. This capability is especially useful in applications such as, but not limited to, the design of pressure sensitive adhesives, coatings and paints, electronic packaging, etc. In addition to providing rapid screening capabilities, the present test method also provides a way of determining reliable, absolute, quantitative measurements of polymer adhesion. This information is critical to building a knowledge base for future molecular engineering of polymer interfaces.

In addition to the design of pressure sensitive adhesives, coatings and paints, and electronic packaging noted above, the methods of the present invention are applicable to numerous other industries, including, but not limited to, formulators, automotive manufacturers, paint producers, release-agent manufacturers, and pressure-sensitive adhesive manufacturers. For example, formulators could use the techniques of the present invention to quickly identify trends in adhesive strength that could be used to design more appropriate materials. The automotive industry could use the techniques of the present invention to identify the preferred polymer candidates for adhesives used in an automobile's interior components. The techniques of the present invention could be useful in the paint industry to help identify blends that possess optimal compositions that withstand certain/different environmental conditions. A more direct application for the techniques of the present invention can be realized by the pressure-sensitive adhesives industry where composition blends, thickness, temperature, humidity, and many more variables play a dominant role in the overall function of their products. Combinatorial measurements of adhesion strength using the principles of the present invention in these and other industries will not only expedite the empirical determination of the proper adhesive materials for a given application, but they will significantly aid in the development of a fundamental understanding of the adhesive properties of polymers which companies can use to guide future product development.

Other features and characteristics of the present invention will become apparent from the following non-limiting examples.

EXAMPLE 1

Measurement of the Adhesion of Polystyrene, a Glassy Polymer, to Itself as a Function of Processing Temperature and Coating Thickness Combinatorial Library Components Substrate: Silicon wafer coated with a 30 nm thick film of polystyrene (PS). Microlens array: Crosslinked polydimethylsiloxane (PDMS) microlens array fabricated by using a mold-casting technique. This microlens array was planar and coated with a thin film of polystyrene that had a gradient in film thickness in one direction. This glassy coating was cast on to a glass slide via a flow coating technique, and subsequently floated via a water surface technique on to the glass slide. Upon being floated on the microlens array, the glassy coating was annealed at 75° C. for several hours.

Test Procedure

The PS-coated silicon wafer was placed on a thermal gradient stage that was fixed to a translation stage of an upright optical microscope. The thermal gradient stage was heated to establish a temperature gradient from 75° C. to 90° C. across a 1.0 centimeter region of the PS-coated silicon wafer. A personal computer was used to control a linear stepping actuator to translate the microlens array into normal contact with the PS-coated silicon wafer. The gradient in coating thickness on the microlens array was arranged orthogonal to the applied temperature gradient on the PS-coated silicon wafer. An optical microscope objective was used to monitor the contact area growth of each individual microlens and record optical images digitally through a CCD camera connected to the personal computer. The applied displacement was monitored with an optical encoder connected to the linear stepping motor. After the microlens array reached an arbitrarily determined maximum contact, the direction of the linear stepping motor was reversed. Applied displacement was monitored together with the decrease in contact area for each microlens.

Analysis

Qualitative: For this test, a critical temperature for a given coating thickness exists at which the PS-coating on the microlens array fails. Failure was determined by the deposition of a "weld" spot on to the PS-coated silicon wafer. This "weld" spot is the region of contact for a given microlens where a crack propagates through the thickness of the coating rather than along the established polystyrene/polystyrene interface. After the test was completed, these "weld" spots were optically visible on the surface of the PS-coated silicon wafer. The boundary of the "weld" spot region defines the critical temperature as a function of coating thickness for failure of the glassy polymer coating.

Quantitative: To quantitatively measure the adhesion energy as a function of temperature and coating thickness and the critical interfacial strength for coating failure, the contact area history for each microlens was measured and contact radius was correlated with applied displacement. With the contact radii, displacement values, and the mechanical properties of the PDMS microlens array, the JKR theory was used to calculate the adhesion energy as a function of temperature and thickness.

Discussion of Results

The results of this test provided a quick assessment of the critical parameters for engineers that are designing insulating and bonding layers in electronic packaging. In addition to the quick, qualitative benefits, this test also provided quantitative data in terms of interfacial adhesion energy that can be correlated to the molecular properties of the polymer coating and substrate. This quantitative understanding permits scientific understanding to further guide the development of new coating materials. Also note that during a single test all microlenses are exposed to the same environmental conditions thus decreasing sample to sample variance that is typically encountered with conventional testing methods.

EXAMPLE 2

Determination, as Function of Surface Energy, the Critical Separation Distance at Which Two Materials are Attracted to Each Other and the Dynamics of this Contact Process Combinatorial Library Components Complementary substrate: Glass slide coated with a self-assembled monolayer of given surface energy.

Microlens library: Crosslinked polydimethylsiloxane (PDMS) microlens array was fabricated by using a mold-casting technique. The microlens array for this test was not planar, but rather the microlenses were distributed on a convex surface of given curvature.

Test

The microlens array was held above an inverted optical microscope with a piezoelectric stepper actuator. The surface-modified glass slide was placed onto the inverted optical microscope's translation stage. The microlens array was moved at a rate of 4 nm/s toward the glass slide. The applied displacement rate was monitored with a fiber optic displacement sensor. The change in interference rings between the microlens and glass slide was monitored through the microscope objective. The microscope objective images were recorded with an attached CCD camera that was controlled by a personal computer. Upon initial contact of the microlens array with the surface-modified glass slide, movement of the microlens array stopped and the changes in contact area were recorded with the CCD camera. After an equilibrium contact area has was achieved, the direction of the stepper actuator was reversed and the microlens array was removed from the glass slide while changes in contact area were recorded with the CCD camera. The curvature of the backing for the microlens array was then changed and this test was repeated.

Analysis

Qualitative: By changing the curvature of the microlens array backing and monitoring the number of microlenses in contact at a given displacement, the critical separation distance for surface attraction was determined. At small degrees of curvature, the number of microlenses in contact change as function of time for a fixed displacement. This change is due to the attractive forces between the two contacting materials. At larger degrees of curvature, the number of microlenses in contact remains static at a fixed displacement for these elastic materials.

Quantitative: By using the pattern of interference rings, the exact separation distance at initial contact were determined. Since the elastic modulus of the microlens material is known, the quantity of force being exerted during initial contact can be calculated. The adhesion energy can also be calculated as a function of surface energy and time of contact using the JKR theory.

Discussion of Results

These results allow for understanding the engineering design of surface coatings that can be used to increase efficiency in microelectromechancial systems (MEMS). This test can also can be used to gain understanding into the surface energetic environment that a biological cell senses as it is approaching a surface. The configuration and subsequent analysis of this test also demonstrates the capability of using each microlens as an individual force transducer. This example also demonstrates the usefulness of not using planar microlens arrays for all tests.

EXAMPLE 3

Determination of the Adhesion Energy of an Ultraviolet (UV) Crosslinkable Elastomer as a Function of Ultraviolet Exposure Time and Thickness of the Elastomer Combinatorial Library Components Complementary substrate: Silicon wafer coated with an UV crosslinkable elastomer. The elastomer coating was cast using a flow coating technique to create a gradient in coating thickness in one direction. Orthogonal to the thickness gradient, a narrow beam of UV light was accelerated across the elastomer coating. By using a linear acceleration for the movement of the UV light beam, a linear gradient in UV exposure time was created orthogonal to the thickness gradient. This process yields an elastomer library of thickness and UV exposure.

Microlens library: A planar fused silica microlens array.

Test

The microlens array was held above an inverted optical microscope with a piezoelectric stepper actuator. The elastomer library was placed onto the inverted optical microscope's translation stage. The microlens array was moved at a rate of 1 $\mu$m/s into contact with the elastomer library. The applied displacement rate was monitored with a fiber optic displacement sensor. The change in contact area of each microlens was monitored as contact was established. Upon reaching a arbitrary maximum contact, the direction of the stepper actuator was reversed and the microlens array was removed from the elastomer library. All contact area images were recorded with a CCD camera that was connected to a personal computer.

Analysis

Qualitative: The relative differences in the displacement at detachment provides a relative measurement of adhesion differences across the elastomer library. In other words, the microlenses that detached first were probing the weakest interface combination of UV exposure and thickness, while the last microlenses to detach probed the strongest interface in the UV vs. thickness library. This qualitative analysis was dependent upon the ability to properly align the planar microlens array with the planar elastomer library.

Quantitative: Refer to Example 1

Discussion of Results

These examples demonstrate how the combinatorial adhesion test method can be used to quickly determine the optimal material and geometric parameters for designing the adhesion characteristics of a new material. Most importantly, this example demonstrates that the microlens array does not need to be soft, but can be made from rigid materials such as fused silica or a metal.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above.

What is claimed is:

1. A method of measuring the adhesive strength of a polymer interface which comprises the steps of:
    a) providing a lens array having a plurality of individual lens elements on a surface thereof;
    b) providing a substrate;
    c) applying a polymer to at least one of the individual lens elements of the lens array or the substrate;
    d) contacting the individual lens elements of the lens array and the substrate in a controlled manner;
    e) separating the individual lens elements of the lens array and the substrate in a controlled manner;
    f) monitoring changes in contact area of the individual lens elements during at least one of steps d) or e); and
    g) calculating the adhesive strength of the polymer at the contact area, wherein the step c) of applying the polymer comprises varying at least one of a thickness and a composition of the polymer across the one of the individual lens elements of the lens array or the substrate.

2. A method of measuring the adhesive strength of a polymer interface according to claim 1, wherein varying the composition of the polymer comprises varying an amount of at least one component of the polymer.

3. A method of measuring the adhesive strength of a polymer interface according to claim 1, wherein the polymer is applied to the individual lens elements of the lens array.

4. A method of measuring the adhesive strength of a polymer interface according to claim 1, wherein changes in contact area of the individual lens elements are optically monitored.

5. A method of measuring the adhesive strength of a polymer interface according to claim 1, wherein at least one of the lens array and the substrate is non-planar.

6. A method of measuring the adhesive strength of a polymer interface according to claim 1, wherein the step contacting the lens array and substrate in a controlled manner comprises moving the lens array with respect to the substrate.

7. A method of measuring the adhesive strength of a polymer interface according to claim 1, wherein the individual lens elements have convex surfaces.

8. A method of measuring the adhesive strength of a polymer interface according to claim 1, wherein the individual lens elements have a shape selected from the group consisting semi-spherical, frusto-conical, cylindrical, trapezoidal and frusto-pyramidal shapes.

9. A method of measuring the adhesive strength of a polymer interface according to claim 1, wherein at least one of the lens array and the substrate is made from a metal or ceramic and does not have the polymer applied thereto.

10. A method of measuring the adhesive strength of a polymer interface which comprises the steps of:
    a) providing a lens array having a plurality of individual lens elements on a surface thereof;
    b) providing a substrate;
    c) applying a polymer to at least one of the individual lens elements of the lens array or the substrate;
    d) providing at least one of a physical gradient, an environmental gradient, and a material gradient across an interface between the lens array and substrate;
    e) contacting the individual lens elements of the lens array and the substrate in a controlled manner;
    f) separating the individual lens elements of the lens array and the substrate in a controlled manner;
    g) monitoring changes in contact area of the individual lens elements during at least one of steps d) or e); and
    h) calculating the adhesive strength of the polymer at the contact area.

11. A method for measuring the adhesive strength of polymer material interfaces that are arranged in a combinatorial library which comprises the steps of:
    a) providing a lens array having a plurality of individual lens elements on a surface thereof;
    b) providing a substrate;
    c) contacting the individual lens elements of the lens array with the substrate in a controlled manner while providing a parameter gradient there between, said parameter gradient comprising at least one of a physical parameter, an environmental parameter and a material parameter; and
    d) calculating the adhesive strength of the polymer at the contact areas, wherein the step of providing a parameter gradient between the lens array and the substrate comprises applying a polymer material to at least one of each of the individual lens elements of the lens array or to the substrate.

12. A method for measuring the adhesive strength of polymer material interfaces that are arranged in a combinatorial library according to claim 11, wherein the step of providing a parameter gradient between the lens array and the substrate comprises applying a pattern of different polymer material to one of the individual lens elements of the lens away or the substrate.

13. A method for measuring the adhesive strength of polymer material interfaces that are arranged in a combinatorial library which comprises the steps of:
    a) providing a lens array having a plurality of individual lens elements on a surface thereof;
    b) providing a substrate;
    c) contacting the individual lens elements of the lens array with the substrate in a controlled manner while providing a parameter gradient there between, said parameter gradient comprising at least one of a physical parameter, an environmental parameter and a material parameter; and
    d) calculating the adhesive strength of the polymer at the contact areas, wherein the step of providing a parameter gradient between the lens array and the substrate comprises providing a gradient of strain between the lens array and the substrate.

14. A method for measuring the adhesive strength of polymer material interfaces that are arranged in a combinatorial library which comprises the steps of:
    a) providing a lens array having a plurality of individual lens elements on a surface thereof;
    b) providing a substrate;
    c) contacting the individual lens elements of the lens array with the substrate in a controlled manner while providing a parameter gradient there between, said parameter gradient comprising at least one of a physical parameter, an environmental parameter and a material parameter; and
    d) calculating the adhesive strength of the polymer the contact areas, wherein the step of providing a parameter gradient between the lens array and the substrate comprises controlling an environmental condition at an interface between the lens array and the substrate.

15. A method for measuring the adhesive strength of polymer material interfaces that are arranged in a combinatorial library which comprises the steps of:
    a) providing a lens array having a plurality of individual lens elements on a surface thereof;
    b) providing a substrate;
    c) contacting the individual lens elements of the lens array with the substrate in a controlled manner while providing a parameter gradient there between, said parameter gradient comprising at least one of a physical parameter, an environmental parameter and a material parameter; and
    d) calculating the adhesive strength of the polymer at the contact areas, wherein changes in contact area of the individual lens elements are optically monitored.

16. A method for measuring the adhesive strength of polymer material interfaces that are arranged in a combinatorial library which comprises the steps of:
    a) providing a lens array having a plurality of individual lens elements on a surface thereof;
    b) providing a substrate;
    c) contacting the individual lens elements of the lens array with the substrate in a controlled manner while providing a parameter gradient there between, said parameter gradient comprising at least one of a physical parameter, an environmental parameter and a material parameter; and d) calculating the adhesive strength of the polymer at the contact areas, wherein at least one of the lens array and the substrate is non-planar.

17. A test device for measuring the adhesive strength of polymer materials that are arranged in a combinatorial library which comprises: a substrate having opposed surfaces; and a polymer material applied to one of the opposed surfaces of the substrate so that the composition of the polymer material varies along at least one direction across the one opposed surface of the substrate, wherein the one opposed surface of the substrate is provided with an array of lens elements.

* * * * *